United States Patent [19]

Metziger et al.

[11] Patent Number: 5,952,383
[45] Date of Patent: Sep. 14, 1999

[54] PHARMACEUTICAL COMPOSITION FOR ORAL DELIVERY

[75] Inventors: Pierre Metziger, Lampertheim, France; Avraham Cohen, Tel Aviv, Israel

[73] Assignee: Negma-Steba International Development N.V., Den Haag, Netherlands

[21] Appl. No.: 09/029,073

[22] PCT Filed: Jun. 30, 1997

[86] PCT No.: PCT/EP97/03405

§ 371 Date: Mar. 3, 1998

§ 102(e) Date: Mar. 3, 1998

[87] PCT Pub. No.: WO98/01118

PCT Pub. Date: Jan. 15, 1998

[30] Foreign Application Priority Data

Jul. 4, 1996 [NL] Netherlands ............................ 1003503

[51] Int. Cl.$^6$ .................................................. A61K 31/19
[52] U.S. Cl. ............................................................ 514/569
[58] Field of Search ................................................ 514/569

[56] References Cited

U.S. PATENT DOCUMENTS

| 5,225,192 | 7/1993 | Lovrecich | 424/78.02 |
| 5,430,067 | 7/1995 | Gallagher et al. | 514/569 |

FOREIGN PATENT DOCUMENTS

| 0243968 | 11/1987 | European Pat. Off. . |
| 0264989 | 4/1988 | European Pat. Off. . |
| 0364944 | 4/1990 | European Pat. Off. . |
| 0519428 | 12/1992 | European Pat. Off. . |
| 0598337 | 5/1994 | European Pat. Off. . |
| 2508798 | 1/1983 | France . |

*Primary Examiner*—Phyllis G. Spivack
*Attorney, Agent, or Firm*—Foley & lardner

[57] ABSTRACT

Pharmaceutical compositions for oral administration are disclosed containing a medicinal product that is insoluble or sparingly soluble in water and oils selected from diacerein, rhein and one of their pharmaceutically acceptable salts.

13 Claims, No Drawings

PHARMACEUTICAL COMPOSITION FOR ORAL DELIVERY

This case is a 371 of PCT/EP97/03405 filed Jun. 30, 1997.

BACKGROUND OF THE INVENTION

1. Field of the Invention

The present invention relates to a pharmaceutical composition adapted for oral administration, and more particularly a pharmaceutical composition adapted for an active principle of a medicinal product for human or veterinary use, which is insoluble or sparingly soluble in water and oils, such as diacerein (diacetylrhein), rhein or one of their salts, which allows their bioavalability to be improved.

2. Description of Related Art

Diacerein, described in patent FR-A-2,508,798, is a compound whose pharmacological properties have been known for several years and have allowed it to be used as a non-steroidal antiinflammatory medicinal product applicable in the treatment of diseases such as arthrosis. However, diacerein is virtually insoluble in water and in alcohols, this being a drawback for its administration, in particular by injection. Moreover, when it is administered orally, diacerein is not totally absorbed by the digestive tract, and, on account of this incomplete absorption, undesirable side effects may be observed, for example laxative effects.

Various derivatives, pharmaceutical compositions and pharmaceutical forms intended to improve the properties of diacerein or of other medicinal products which are insoluble or sparingly soluble in water have been described in the literature. Thus, for example, patent EP-A-243,968 describes a water-soluble potassium salt of diacerein which can be used in the preparation of compositions for parenteral administration.

Patent EP-A-598,337 describes a composition comprising an active principle of a medicinal product which is insoluble or sparingly soluble in water, incorporated into a crosslinked polymer, a surfactant and an oil, this composition being of improved bioavailability. U.S. Pat. No. 5,225,192 describes a process for preparing a fast-dissolving medicinal product, which consists in incorporating the medicinal product into crosslinked polymer particles which are insoluble but capable of swelling in water, in leaving the product in contact with an organic solvent and in drying under vacuum.

The subject of the present invention is a pharmaceutical composition adapted for an active principle of a medicinal product for human or veterinary use, containing a medicinal product which is insoluble or sparingly soluble in water and oils, in particular diacerein, rhein or one of their salts, which can be administered orally and affords faster and more complete absorption of the active principle into the body, and being of better bioavailability, thus making it possible to reduce or eliminate the abovementioned side effects.

The subject of the present invention is also a novel pharmaceutical composition based on diacerein, rhein or diacerein or rhein salts, which can be administered orally in the form of a wafer capsule or a gelatin capsule, and which is of improved bioavalability when compared with the usual forms.

DETAILED DESCRIPTION OF PREFERRED EMBODIMENTS

The pharmaceutical composition according to the present invention, which can be administered orally, containing the abovementioned medicinal product that is insoluble or sparingly soluble in water and oils, selected from diacerein, rhein or one of their pharmaceutically acceptable salts, is essentially distinguished in that it comprises

- a liquid support oil selected from a plant, animal or mineral oil
- a suspension agent,
- a homogenizing agent,
- a surfactant, and
- one or more pharmaceutically acceptable excipients or supports.

The pharmaceutically acceptable salts which can be used in the invention can be, for example, the sodium or potassium salts of diacerein or of rhein.

The liquid support oil used in the composition of the invention can be selected from a plant oil (for example ground-nut oil, soybean oil or sunflower oil), a mineral oil (for example a paraffin) and an animal oil. It can consist of one or more medium-chain triglycerides. The expression "medium-chain" used here with reference to triglycerides means a linear or branched chain preferably comprising between 8 and 12 carbon atoms approximately. Needless to say, it is possible to use one or more triglycerides in combination. The medium-chain triglyceride used in the composition of the invention can be, for example, a fractionated coconut oil.

The suspension agent used in the composition can be any oil which is solid or semi-solid at room temperature, and, for example, a hydrogenated plant oil, a wax (for example beeswax) or a gelling agent (for example a silica). According to the invention, a totally or partially hydrogenated plant oil is preferably used, for example hydrogenated soybean oil.

The surfactant can be an anionic or nonionic surfactant but it is preferably a nonionic surfactant chosen from polyalkyl sorbitan esters, polyoxyethylene sorbitan derivatives, and for example a monooleic ester of polyhydroxyethyl sorbitan such as Polysorbate 80 (or Tween 80®), or Span®. These surfactants are well known in the pharmaceutical field and are commercially available.

The homogenizing agent can be chosen from the agents currently used in the art. According to the invention, soybean lecithin is preferably used, which has the advantage of exerting both a homogenizing action and a fluidizing action on the components used.

The amounts of the various components of the composition according to the invention can be adjusted as a function of the desired effects and of the active principle of the medicinal product used.

In the case of diacerein and rhein, it can be particularly advantageous to use a composition comprising between 5 and 25% by weight, preferably between 5 and 10% by weight, of homogenizing agent, and between 5 and 25% by weight, preferably between 10 and 15% by weight, of surfactant, relative to the total weight of the components and of the active principle.

The weight ratio between the liquid support oil and the suspension agent is between 8:1 and 2:1, and it is preferably close to 4:1. These two components can be mixed together at room temperature or under hot conditions during the preparation of the composition in order to form a paste or an ointment. The temperature is adjusted as a function of the nature of the components used.

The above components are mixed with the active principle of the medicinal product according to the techniques usually used for pharmaceutical preparations, by adding thereto, where appropriate, various common excipients and additives for pharmaceutical formulation.

For example, in the case of a liquid support oil consisting of medium-chain triglycerides and a suspension agent consisting of a hydrogenated soybean oil, combined with soybean lecithin as homogenizing agent, the process is preferably performed in the following way: triglycerides are heated to a temperature of 65°–70° C. approximately, the soybean oil is melted therein and, after cooling to room temperature, the soybean lecithin and a nonionic surfactant are added and the mixture is homogenized in a mixer of standard type, after which the diacerein is added and homogenization of the mixture is continued for 10 to 30 minutes.

The composition according to the invention can advantageously be in the form of soft gelatin capsules or in the form of hard gelatin capsules, containing, for example, between 20 and 50 mg of active principle per unit.

The soft and hard gelatin capsules are prepared according to the usual pharmaceutical techniques and can include, for example, a gelatin-based wall containing various additives such as glycerol, titanium dioxide or iron oxide. It is particularly advantageous for the wall of the gelatin capsules to contain a substance capable of isolating the composition from any source of moisture which might lead to degradation of the active principle. A silicone oil, and for example dimethicone, can be used.

In the case of diacerein, which is virtually insoluble in water and ethanol and sparingly soluble in carbonate solutions and in tetrahydrofuran, the composition according to the invention affords a substantial improvement in the pharmacokinetic properties. In particular, in the case of an oral administration in the form of soft or hard gelatin capsules containing the composition of the invention, an appreciable increase in the rate of dissolution and in the maximum concentration obtained, when compared with a standard composition in the form of a hard gelatin capsule, is observed.

The results of the clinical studies in man, in the case of a composition in capsules containing a 38 mg dose of diacerein, compared with a standard pharmaceutical form (hard gelatin capsule) containing a 50 mg dose of diacerein, are summarized in the table below:

| Comparative table | | |
|---|---|---|
| | Hard gelatin capsule | Invention |
| $C_{max}$ (mg/ml) | 2.07 ± 0.57 | 4.38 ± 1.34 |
| $T_{max}$ (h) | 4.30 ± 1.65 | 1.30 ± 0.48 |

It is seen that the composition according to the present invention affords a plasma concentration ($C_{max}$) that is markedly increased, more than doubled, in a much shorter time ($T_{max}$) since the time falls from 4.3 hours to about 1.3 hours. Furthermore, it is observed that the values of the AUC (area under the curve) are increased by more than 25%. These results show that the bioavailability of the active principle used (diacerein) is markedly improved.

Examples of compositions and of pharmaceutical forms for oral administration in accordance with the present invention are given below in order to illustrate the invention without limiting its scope.

EXAMPLE 1

A composition is prepared containing:

| medium-chain triglycerides | 156 mg |
|---|---|
| hydrogenated soybean oil | 38 mg |
| soybean lecithin | 14.5 mg |
| Polysorbate 80 | 43.5 mg |

This composition is mixed carefully with 38 mg of diacerein in a disk mixer (400 revolutions/min.; 30 min), and encapsulated in the usual manner in capsules based on gelatin, glycerol, purified water and Anidrisorb® supplemented with titanium oxide and iron oxide.

EXAMPLE 2

A composition identical to that of Example 1 above, containing 38 mg of diacerein, is encapsulated in gelatin capsules whose wall composition comprises the components indicated in Example 1 as well as 15% by weight approximately of dimethicone.

EXAMPLE 3

A hard gelatin capsule containing a 30 mg dose of rhein sodium salt is prepared using a composition containing:

| fractionated coconut oil | 140 mg |
|---|---|
| soybean oil | 35 mg |
| soybean lecithin | 10 mg |
| Span ® (sorbitan ester) | 30 mg |

This composition is mixed carefully with 30 mg of rhein sodium salt and introduced into hard gelatin capsules with a wall made of gelatin, of the usual commercial type.

We claim:

1. Pharmaceutical composition for oral administration containing a medicinal product that is insoluble or sparingly soluble in water and oils, selected from diacerein, rhein and one of their pharmaceutically acceptable salts, comprising:
a liquid support oil selected from a plant, animal or mineral oil,
a suspension agent,
a homogenizing agent,
a surfactant,
and one or more pharmaceutically acceptable expedients or supports.

2. Composition according to claim 1, wherein the liquid support oil is one or more triglycerides with a linear or branched medium chain of 8 to 12 carbon atoms.

3. Composition according to claim 1, wherein the suspension agent is a totally or partially hydrogenated plant oil.

4. Composition according to claim 3, wherein the hydrogenated plant oil is hydrogenated soybean oil.

5. Composition according to claim 1, wherein the surfactant is a nonionic surfactant selected from polyalkyl sorbitan esters and polyoxyethylene sorbitan derivatives.

6. Composition according to claim 1, wherein the homogenizing agent is soybean lecithin.

7. Composition according to claim 1, comprising between 5 and 10% by weight of homogenizing agent and between 10 and 15% by weight of surfactant, relative to the total weight of the components and of an active principle.

8. Composition according to claim 1, wherein the weight ratio between the liquid support oil and the suspension agent is between 8:1 and 2:1.

9. Composition according to claim 1, wherein the composition is in the form of a soft gelatin capsule.

10. Composition according to claim 9, wherein a wall of the soft gelatin capsule contains dimethicone.

11. Composition according to claim 1, wherein the composition is in the form of a hard gelatin capsule.

12. Composition according to claim 11, wherein the wall of the hard gelatin capsule contains dimethicone.

13. Composition according to claim 1, wherein an active principle of a medicinal product is diacerein.

* * * * *